United States Patent [19]

Iwamoto et al.

[11] Patent Number: 5,120,719
[45] Date of Patent: Jun. 9, 1992

[54] CONJUGATE OF PROSTAGLANDIN AND POLYSACCHARIDE

[75] Inventors: Kiyoshi Iwamoto; Masahiro Kawahara; Sumio Watanabe; Yasuo Miyake; Fumio Sagami, all of Ibaraki, Japan

[73] Assignee: Eisai Co., Ltd., Tokyo, Japan

[21] Appl. No.: 437,463

[22] Filed: Nov. 15, 1989

[30] Foreign Application Priority Data

Nov. 18, 1988 [JP] Japan .................. 63-291945
Oct. 30, 1989 [JP] Japan .................. 1-282810

[51] Int. Cl.⁵ ............. A61K 31/557; A61K 31/715; A61K 31/72
[52] U.S. Cl. .................. 514/54; 514/573; 536/4.1; 536/2; 536/63; 536/110; 536/112; 536/119
[58] Field of Search ......... 514/573, 54; 536/4.1, 536/2, 63, 110, 112, 119

[56] References Cited

U.S. PATENT DOCUMENTS

| | | | |
|---|---|---|---|
| 4,036,954 | 7/1977 | Murakami et al. | 514/573 |
| 4,066,787 | 1/1978 | Okazaki et al. | 514/573 |
| 4,092,428 | 5/1978 | Murakami et al. | 514/573 |
| 4,113,882 | 9/1978 | Okazaki et al. | 514/573 |
| 4,352,790 | 10/1982 | Johansson et al. | 514/573 |
| 4,675,182 | 6/1987 | Streuff et al. | 514/690 |

OTHER PUBLICATIONS

Havashi et al.; Chemical Abstracts 84:121295t (1976).
Okazaki et al., Chemical Abstracts 88:158468k (1978).
Ferruti et al.; Chemical Abstracts 89:117800q (1978).
Shimizu et al.; Chemical Abstracts 90:109952w (1979).
Shimizu et al.; Chemical Abstracts 90:142152h (1979).
Ariga et al.; Chemical Abstracts 92:135437t (1980).
Kawada et al.; Chemical Abstracts 92:169243s (1980).
Johansson et al.; Chemical Abstracts 94:90334e (1981).
Ono Pharm.; Chemical Abstracts 95:30415t (1981).
Lee; Chemical Abstracts 96:223133d (1982).
Streuff et al.; Chemical Abstracts 101:198205r (1984).
Roca Massa et al.; Chemical Abstracts 107:12841r (1987).

Primary Examiner—John W. Rollins
Assistant Examiner—Nancy S. Carson
Attorney, Agent, or Firm—Flynn, Thiel, Boutell & Tanis

[57] ABSTRACT

A conjugate formed by the covalent bonding of a prostaglandin or a similar compound thereto and a polysaccharide. The prostaglandin is selected from prostaglandin E1, prostaglandin E2, prostaglandin F2α, prostaglandin I2, carbacycline and iloprost and the polysaccharide is selected from pluran, amylose, amylopectin, cellulose, dextran and hydroxyethylated starch.

12 Claims, 5 Drawing Sheets

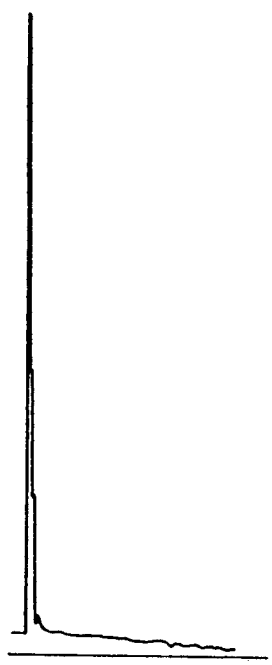
FIG. I(a)
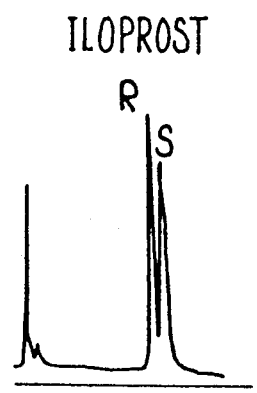
FIG. I(b)
ILOPROST
R
S
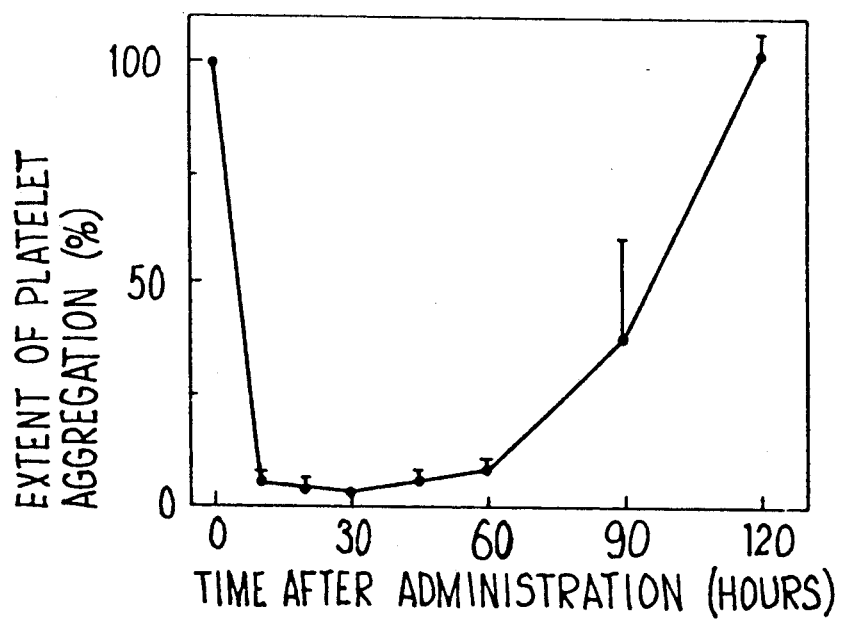
FIG. 3

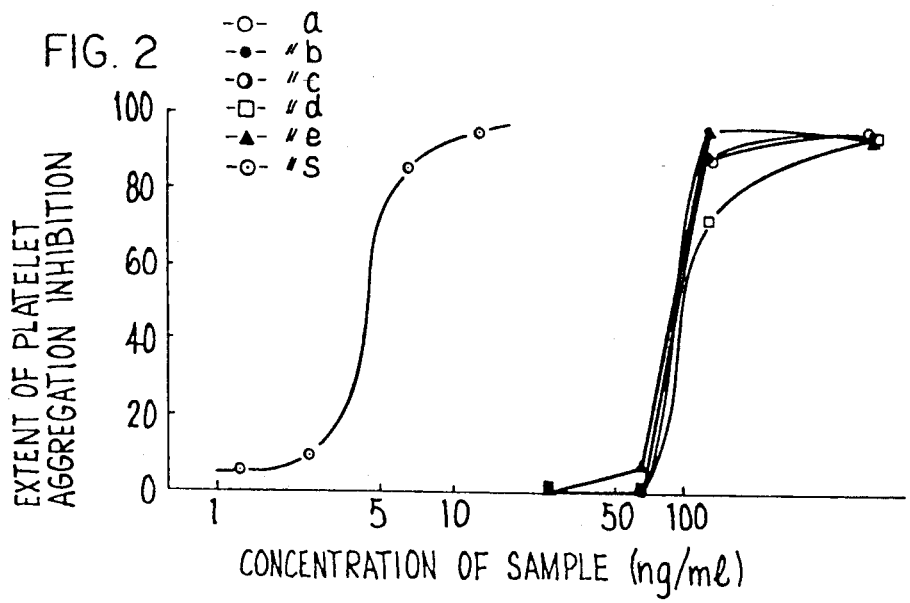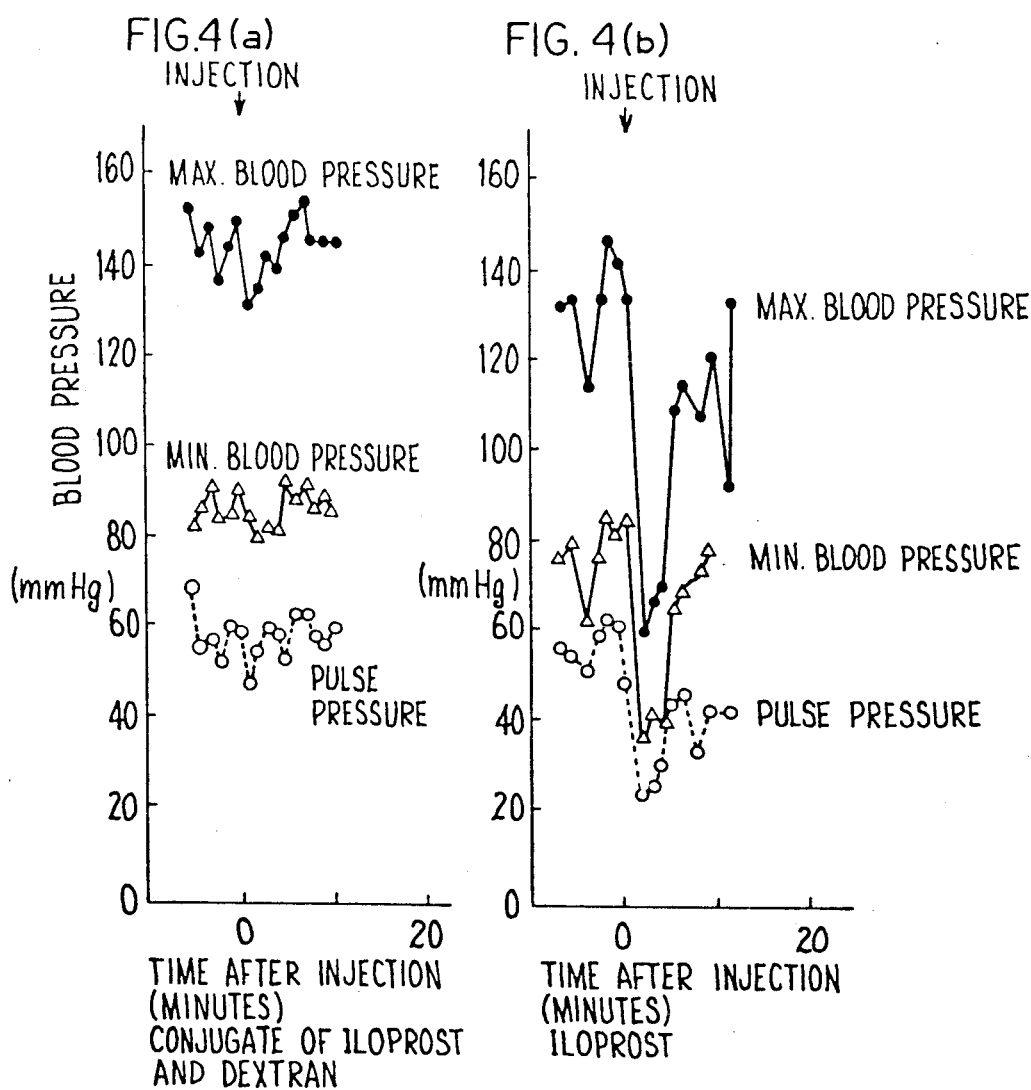

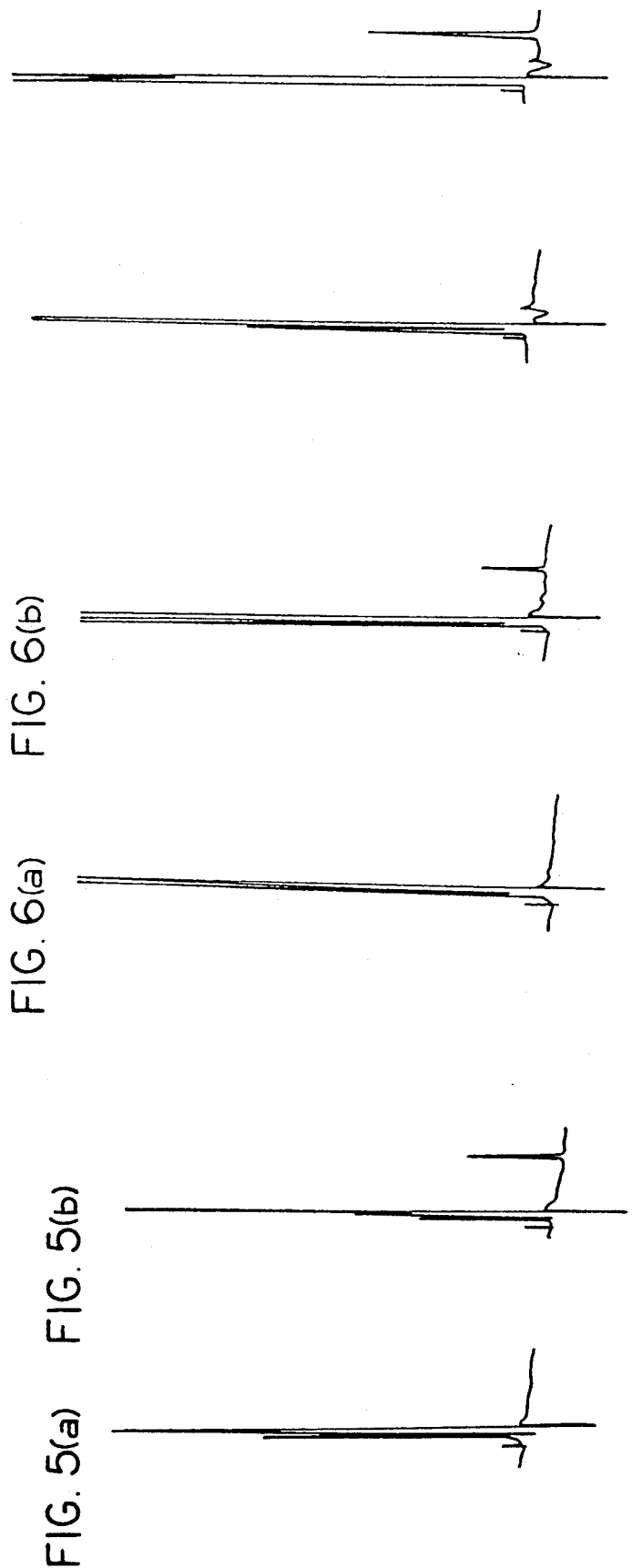

CONJUGATE OF PROSTAGLANDIN AND POLYSACCHARIDE

The invention relates to a conjugate of prostaglandin, or a similar compound thereto, referred to as prostaglandins, and a polysaccharide. In the conjugate of the invention, polysaccharides are incorporated, by covalent bonding, into prostaglandins to serve as a physiologically active substance.

PRIOR ART

Prostaglandins have been confirmed to exist within the body and are known to be compounds that are composed of a skeleton of prostanoic acid having 20 carbon atoms. They are currently recognized for their application in medical and pharmaceutical fields as a result of their pharmacological actions which include inhibition of platelet aggregation, lowering of blood pressure, vasodilation, antiasthmatic effects, inhibition of secretion of stomach acids and promotion of uterine contraction. However, in general, prostaglandins are unstable compounds and possess properties which make them extremely susceptible to decomposition from acids, bases and heat.

On the other hand, prostaglandins are also metabolically unstable and are metabolized and inactivated in the body extremely rapidly by the liver (N. A. Nelson, R. C. Kelly and R. A. Johnson, Chemical & Engineering News, Aug. 16, 30(1982)). In addition, their elimination half-life from the blood is extremely short and their duration of action is also extremely short. As a result, their use in treatment in the clinical setting is primarily through intravenous infusion and it is known that the resulting burden on the patient in terms of dosage is severe. In addition, it has also been reported that the administration of prostaglandins results in a transient drop in blood pressure due to their vasodilatory action (N. A. Nelson, R. C. Kelly and R. A. Johnson, Chemical & Engineering News, Aug. 16, 30(1982)).

Consequently, improvements in terms of both synthesis and preparation of prostaglandins are required for their broad-ranging use as a pharmaceutical product.

In order to solve these types of problems, it is necessary to develop a preparation which is not easily metabolized by the liver and can be made to circulate for an extended period of time in the blood in order to be used as a pharmaceutical product, while also minimizing adverse side-effects.

As a result of earnest studies from the viewpoints described above, the inventors discovered that the above problems could be solved by covalently bonding a polysaccharide to prostaglandin.

In other words, as a result of studies for the purpose of extending the duration of the effects of prostaglandins by restricting the transmigration of prostaglandins into the liver at the time of administration and lengthening their elimination half-life from the blood, the inventors completed this invention by discovering that polysaccharide-prostaglandin complexes obtained by chemical modification achieve the above objectives by covalently bonding prostaglandins with polysaccharides since polysaccharides of a certain molecular weight or greater have a long elimination half-life from the blood (G. Arturson, G. Wallenius; Scandinav, J. & Lab. Investigation, 1, 76(1964)).

In other words, this invention provides a new compound which has the characteristic of being composed of a complex of a prostaglandin, or a similar compound, and a polysaccharide.

The invention provides a conjugate of a prostaglandin, or a compound similar thereto, and a polysaccharide. The conjugate is called hereinafter also a complex.

It is preferable that the prostaglandin, or a compound similar thereto, are selected from the group consisting of prostaglandin E1, prostaglandin E2, prostaglandin F2x, prostaglandin I2, carbacycline and iloprost and the polysaccharide is selected from the group consisting of pluran, amylose, amylopectin, cellulose, dextran and hydroxyethylated starch.

It is preferred that 0.01 to 20 units, in particular 0.05 to 5 units, of prostaglandin, or a similar compound thereto, are bonded to 100 sugar units of a polysaccharide.

A more preferable group of prostaglandin, or a compound similar thereto, include prostaglandin E1, prostaglandin I2, carbacycline and iloprost.

The following provides a detailed description of the invention.

In this invention, examples of prostaglandins or similar compounds include prostaglandin $E_1$ ($PGE_1$), prostaglandin $I_2$ ($PGI_2$), carbacycline, which is a derivative of prostaglandin $I_2$, and iloprost, which is also a derivative of prostaglandin $I_2$.

Examples of the polysaccharides pertinent to this invention include pluran, amylose, amylopectin, cellulose, dextran and hydroxyethylated starch. Those with a molecular weight of 5,000-500,000 are preferable. In addition, since those with a molecular weight of 75,000 are distributed over a molecular weight range of 25,000-150,000 in plasma substitute preparations (G. Arturson, K. Granath, L. Thoren and G. Wallenius, Acta. Chir. Scand., 127, 543(1964), those polysaccharides pertinent to this invention having a molecular weight within a range of 10,000-150,000 are even more preferable.

In this invention, the complex refers to an ester complex resulting from condensation and dehydration between the carboxyl group of the prostaglandin and the hydroxyl group of the polysaccharide. For the prostaglandin-polysaccharide complex in this invention, those complexes in which 0.01-20 prostaglandins are bonded per 100 sugar units which compose the polysaccharide are preferable. Narrower ranges, 0.05 to 10 and 0.05 to 5, are more preferable.

Although preparation of the prostaglandin-polysaccharide complex in this invention involves synthesis by routine dehydration condensation methods, methods which use condensing agents such as dicyclohexylcarbodiimide (DCC) or 1,1'-carbonyldiimidazole (CDI) are convenient (E. Schacht, J. Vermeersch, F. Vandoorne, R. Vercauteren, J. P. Pemon, "Recent Advances in Drug Delivery Systems", J. M. Anderson, S. W. Kim, eds., 245(1986), Plenum Press, London).

The amount of prostaglandin and polysaccharide that is bonded can be varied by changing the amount of reagent which is used. On the other hand, since prostaglandin-polysaccharide conjugates easily decompose in an aqueous solution of sodium hydroxide, an alkaline buffer solution or a hydrolase such as trypsin or chymotrypsin, the amount of prostaglandin and polysaccharide that is bonded can be determined by performing hydrolysis using the above methods and then measuring the amount of free prostaglandin.

In other words, if x is taken to be the number of mg of prostaglandin that is bonded to 1 g of polysaccharide following the bonding of a prostaglandin and a polysaccharide in accordance with the method described in Embodiment 1 to be described later, the number of prostaglandins that are bonded per 100 units of monosaccharides of the polysaccharides can be determined using the following equation:

$$y = \frac{\text{molecular weight of unit monosaccharide of polysaccharide} \cdot x}{\text{Molecular Weight of Bonded Prostaglandin}} \times 0.1$$

BRIEF DESCRIPTION OF DIAGRAMS

FIGS. 1a and 1b indicate the liquid chromatograms of Sample Solutions 1 and 2 of Experimental Example 1.

FIG. 2 is a graph which indicates the measurement results of platelet aggregation as performed in Experimental Example 2.

FIG. 3 is a graph which indicates the measurement results of the duration of the effects of platelet aggregation inhibitory action as performed in Experimental Example 3.

FIGS. 4a and 4b are graphs which indicate changes in blood pressure over time as performed in Experimental Example 4.

FIG. 5 indicates the high-pressure liquid chromatography spectra for the prostaglandin $E_1$-dextran bonded complex of Experimental Example 5 before hydrolysis treatment (a) and after hydrolysis treatment (b).

FIG. 6 indicates the high-pressure liquid chromatography spectra for the prostaglandin $E_2$-dextran bonded complex of Experimental Example 5 before hydrolysis treatment (a) and after hydrolysis treatment (b).

FIG. 7 indicates the high-pressure liquid chromatography spectra for the prostaglandin $F_{2\alpha}$-dextran bonded complex of Experimental Example 5 before hydrolysis treatment (a) and after hydrolysis treatment (b).

Figure 8:
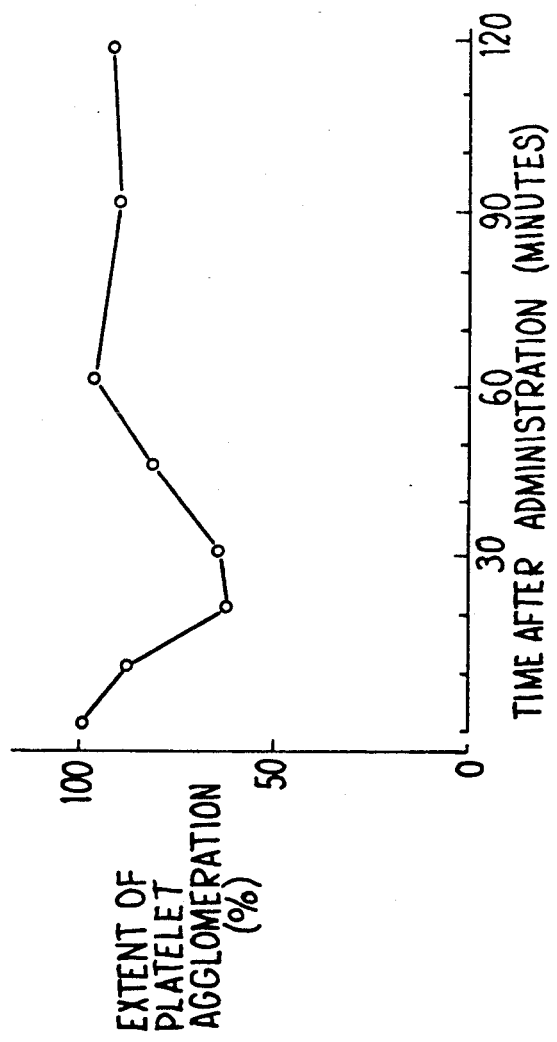

FIG. 8 indicates the duration of platelet aggregation inhibitory effects of the prostaglandin $E_1$-dextran bonded complex of Experimental Example 7.

Figure 9:
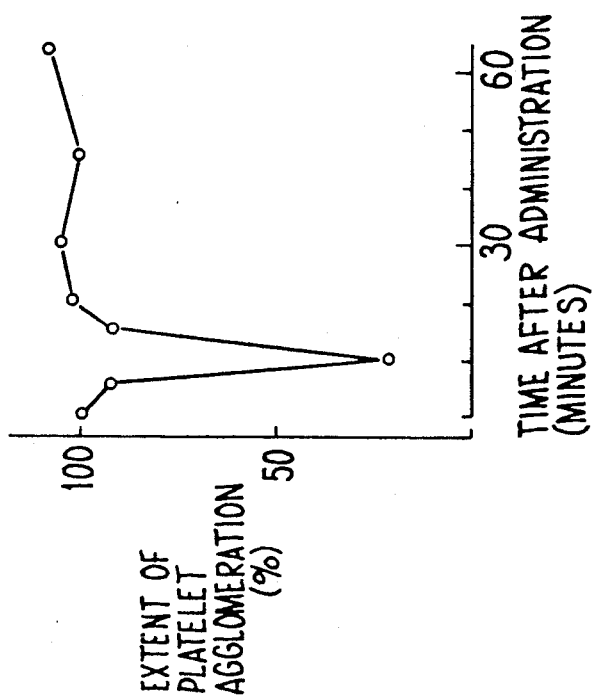

FIG. 9 indicates the platelet aggregation inhibitory effects of prostaglandin $E_1$ (control) of Experimental Example 7.

Figure 10:
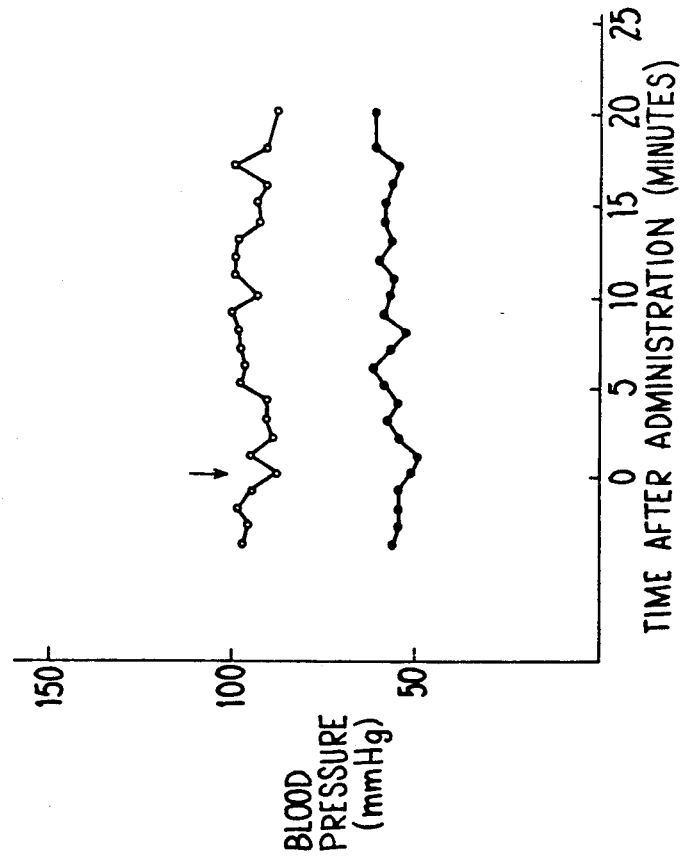

FIG. 10 indicates the influence on blood pressure of the prostaglandin $E_2$-dextran bonded complex of Experimental Example 8.

Figure 11:
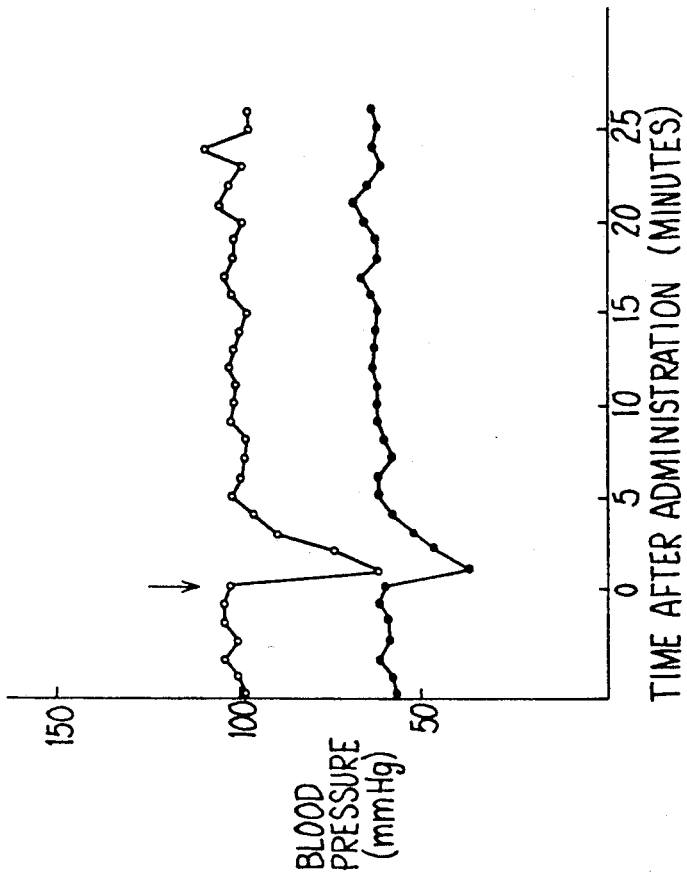

FIG. 11 indicates the influence of blood pressure of prostaglandin $E_2$ (control) of Experimental Example 8.

EMBODIMENTS

Although the following examples provide a detailed description of the invention using specific embodiments, the present invention is not limited to these embodiments.

EMBODIMENT 1

60 mg of iloprost and 28 mg of 1,1'-carbonyldiimidazole (CDI) were mixed in 5 ml of dimethylsulfoxide (DMSO) and stirred for 15 minutes at room temperature. Following this, a solution in which 1 g of dextran (weight average molecular weight: 72,200, Farmacia) and 2.5 mg of 4-pyrrolidinopyridine had been mixed in advance in 30 ml of DMSO and 6 ml of triethylamine was added. This mixture was then stirred for an additional 2 days at room temperature. 500 ml of chilled ethanol was then added to the reaction mixture and the precipitate that formed was filtered off.

After washing the precipitate with 500 ml of chilled ethanol on a glass filter, the precipitate was dried at room temperature under a reduced pressure. The yield was 0.79 g and the amount of iloprost that was bonded as determined by high-pressure liquid chromatography was 0.29 units per 100 sugar units.

The iloprost-dextran complex thus obtained was very soluble in water and insoluble in methanol and ethanol. When $^1$H-NMR measurement was performed on the complex in $D_2O$ solvent, in addition to the peak originating from the dextran, the peaks indicated below which are characteristic of iloprost were also observed.

s = 1.06, 1.13 ppm (3H, d, —$CH_3$ proton bonded to 16 position carbon)

s = 1.91 ppm (3H, s, —$CH_3$ proton bonded to 21 position carbon)

EMBODIMENT 2

70 mg of iloprost and 32 mg of 1,1'-carbonyldiimidazole (CDI) were mixed in 5 ml of dimethylsulfoxide (DMSO) and stirred for 15 minutes at room temperature. Following this, a solution in which 1.2 g of pluran (weight average molecular weight: 50,600, Ringen) and 2.9 mg of 4-pyrrolidinopyridine had been mixed in advance in 35 ml of DMSO and 7 ml of triethylamine was added. This mixture was then stirred for an additional 2 days at room temperature. 500 ml of chilled ethanol was then added to the reaction mixture and the precipitate that formed was filtered off. After further washing the precipitate with 500 ml of chilled ethanol on a glass filter, the precipitate was dried at room temperature under a reduced pressure. The yield was 1.08 g and the amount of iloprost that was bonded as determined by high-pressure liquid chromatography was 0.64 units per 100 sugar units.

The iloprost-pluran complex thus obtained was very soluble in water and insoluble in methanol and ethanol. When $^1$H-NMR measurement was performed on the complex in $D_2O$ solvent, in addition to the peak originating from the pluran, the peaks indicated below which are characteristic of iloprost were also observed.

s = 1.06, 1.13 ppm (3H, d, —$CH_3$ proton bonded to 16 position carbon)

s = 1.91 ppm (3H, s, —$CH_3$ proton bonded to 16 position carbon)

EMBODIMENT 3

60 mg of iloprost and 28 mg of 1,1'-carbonyldiimidazole (CDI) were mixed in 5 ml of dimethylsulfoxide (DMSO) and stirred for 15 minutes at room temperature. Following this, a solution in which 1 g of hydroxyethylated starch (HES, Sigma) and 2.5 mg of 4-pyrrolidinopyridine had been mixed in advance in 50 ml of DMSO and 10 ml of triethylamine was added. This mixture was then stirred for an additional 2 days at room temperature. 500 ml of chilled ethanol was then added to the reaction mixture and the precipitate that formed was filtered off. After further washing the precipitate with 500 ml of chilled ethanol on a glass filter, the precipitate was dried at room temperature under a reduced pressure. The yield was 0.70 g and the amount of iloprost that was bonded as determined by high-pressure liquid chromatography was 0.76 units per 100 sugar units.

The iloprost-hydroxyethylated starch complex thus obtained was very soluble in water and insoluble in methanol and ethanol. When ¹H-NMR measurement was performed on the complex in D₂O solvent, in addition to the peak originating from the hydroxyethylated starch, the peaks indicated below which are characteristic of iloprost were also observed.

s = 1.15 ppm (3H, m, —CH₃ proton bonded to 16 position carbon)

s = 1.97 ppm (3H, m, —CH₃ proton bonded to 21 position carbon)

EMBODIMENT 4

60 mg of iloprost and 28 mg of 1,1'-carbonyldiimidazole (CDI) were mixed in 5 ml of dimethylsulfoxide (DMSO) and stirred for 15 minutes at room temperature. Following this, a solution in which 1.0 g of dextran (weight average molecular weight: 38,800, Farmacia) and 2.5 mg of 4-pyrrolidinopyridine had been mixed in advance in 30 ml of DMSO and 6 ml of triethylamine was added. This mixture was then stirred for an additional 2 days at room temperature. 500 ml of chilled ethanol was then added to the reaction mixture and the precipitate that formed was filtered off. After further washing the precipitate with 500 ml of chilled ethanol on a glass filter, the precipitate was dried at room temperature under a reduced pressure. The yield was 0.96 g and the amount of iloprost that was bonded, as determined by high-pressure liquid chromatography, was 0.32 units per 100 sugar units.

The iloprost-dextran complex thus obtained was very soluble in water and insoluble in methanol and ethanol. When ¹H-NMR measurement was performed on the complex in D₂O solvent, in addition to the peak originating from the dextran, the peaks indicated below, which are characteristic of iloprost, were also observed.

s = 1.06, 1.13 ppm (3H, d, —CH₃ proton bonded to 16 position carbon)

s = 1.91 ppm (3H, d, —CH₃ proton bonded to 16 position carbon)

EMBODIMENT 5

60 mg of iloprost and 28 mg of 1,1'-carbonyldiimidazole (CDI) were mixed in 5 ml of dimethylsulfoxide (DMSO) and stirred for 15 minutes at room temperature. Following this, a solution in which 1.0 g of dextran (weight average molecular weight: 10,900, Farmacia) and 2.5 mg of 4-pyrrolidinopyridine had been mixed in advance in 30 ml of DMSO and 6 ml of triethylamine was added. This mixture was then stirred for an additional 2 days at room temperature. 500 ml of chilled ethanol was then added to the reaction mixture and the precipitate that formed was filtered off. After further washing the precipitate with 500 ml of chilled ethanol on a glass filter, the precipitate was dried at room temperature under a reduced pressure. The yield was 0.97 g and the amount of iloprost that was bonded as determined by high-pressure liquid chromatography was 0.31 units per 100 sugar units.

The iloprost-dextran complex thus obtained was very soluble in water and insoluble in methanol and ethanol. When ¹H-NMR measurement was performed on the complex in D₂O solvent, in addition to the peak originating from the dextran, the peaks indicated below, which are characteristic of iloprost, were also observed.

s = 1.06, 1.13 ppm (3H, d, —CH₃ proton bonded to 16 position carbon)

s = 1.91 ppm (3H, d, —CH₃ proton bonded to 16 position carbon)

The following provides a detailed description of the effectiveness of the invention in experimental examples.

EXPERIMENTAL EXAMPLE 1

200 mg of the powder obtained in Embodiment 1 was dissolved in 1 ml of physiological saline. 0.1 ml of this solution was then accurately removed and to this was added 0.9 ml of physiological saline. 0.1 ml of this solution was again accurately removed and to this was added 0.9 ml of a mixed solution of acetonitrile and pH 3 aqueous phosphoric acid (volume ratio: 34/66) to accurately bring the solution to 1 ml. The resulting solution was then used as Sample Solution 1.

Similarly, 200 mg of the powder obtained in Embodiment 1 was dissolved in 1 ml of physiological saline. 0.1 ml of this solution was then accurately removed and to this was added 0.9 ml of 0.1N sodium hydroxide solution to accurately bring the solution to 1 ml. This solution was then allowed to stand for 30 minutes at room temperature. 0.1 ml of this solution was then again accurately removed and to this was added 0.9 ml of a mixed solution of acetonitrile and pH 3 aqueous phosphoric acid to accurately bring the solution to 1 ml. The resulting solution was then used as Sample Solution 2.

The presence of iloprost in Sample Solutions 1 and 2 was then confirmed by high-pressure liquid chromatography and the iloprost-dextran complex was measured.

HPLC Conditions:

Solid Phase: Nucleosil C₁₈ (3 um) (4.6 mmϕ × 50 mm)

Mobile Phase: Acetonitrile-pH 3 Phosphoric Acid Buffer Solution = 34:16

Flow Rate: 1 ml/min.

Detection Target: 207 nm

Injection Amount: 20 ul

Those results are indicated in FIG. 1.

In FIG. 1, (a) indicates the chromatogram of Sample Solution 1 and (b) indicates the chromatogram of Sample Solution 2.

In other words, (a) indicates the iloprost-dextran complex indicating that there is no free iloprost present. In addition, (b) indicates the free iloprost peak that results from hydrolysis of the iloprost-dextran complex.

Furthermore, the amount of iloprost and dextran that is bonded is such that 0.29 units of iloprost were contained per 100 sugar units which compose the dextran.

EXPERIMENTAL EXAMPLE 2

Platelet Aggregation Inhibitory Effects 100 mg of each of the powders of the iloprost-polysaccharide complexes obtained in Embodiments 1-5 were respectively weighed out. To each of these, physiological saline was added to make solutions having iloprost concentrations of 30 ng/ml to 50 ng/ml. These solutions were then used as Sample Solutions a-e.

Separate from the above solutions, 100 mg of iloprost was weighed out and a solution having an iloprost concentration of 1 ng/ml to 10 ng/ml was prepared using physiological saline. This solution was then used as the standard solution s. 200 ul of platelet-rich plasma (PRP) from the blood obtained from a beagle using routine methods was then placed in an aggregometer cell followed by the respective addition of 25 ul each of Sample Solutions a-e and standard solution s. These mixtures were then immediately incubated at 37° C. for 3 minutes. Following incubation, 25 ul of 300 uM ADP (adenosine diphosphate) was added to each of the mixtures and the extent of platelet aggregation of each of the mixtures was then measured using an aggregometer.

Those results are indicated in FIG. 2.

FIG. 2 indicates the concentration effects of beagle platelet aggregation inhibition of Samples a-e and Standard Solution s.

In FIG. 2, —○— indicates the platelet aggregation inhibition of Sample a, —●— indicates that of Sample b, —◐— indicates that of Sample c, —□— indicates that of Sample d, —▲— indicates that of Sample e and —⊙— indicates that of Standard s.

It can be seen from FIG. 2 that although weaker in comparison to that of iloprost, the iloprost-polysaccharide complex demonstrates platelet aggregation inhibitory effects.

EXPERIMENTAL EXAMPLE 3

Duration of Platelet Aggregation Inhibitory Effects 2.0 g of the iloprost-dextran complex obtained in Embodiment 1 were weighed out and to this was added physiological saline to accurately bring the solution to 100 ml. This was used as the sample solution.

5 ml of the above sample solution was then injected over the course of 1 minute into the cephalic vein of the right forelimb of a female beagle (body weight: 10.6–12.6 kg). Following injection, 4.5 ml of blood was drawn over time from the cephalic vein of the right forelimb using a 0.5 ml syringe containing 3.8% sodium citrate.

225 ul of platelet-rich plasma (PRP) obtained using routine methods from the blood which was drawn from the beagle was placed in an aggregometer cell and incubated for 3 minutes at 37° C. Following incubation, 25 ul of 200 uM ADP was added and platelet aggregation was measured using the aggregometer.

The changes over time in platelet aggregation inhibitory effects following intravenous injection of the samples are indicated in FIG. 3.

According to FIG. 3, it is clear that the duration of platelet aggregation inhibitory effects of the sample is roughly 1.5 hours.

EXPERIMENTAL EXAMPLE 4

Fluctuations in Blood Pressure 2.0 g of the iloprost-dextran complex obtained from Embodiment 1 was weighed out and accurately brought to 100 ml by the addition of physiological saline. This solution was then used as the sample solution.

5 ml of the above sample solution was then injected over the course of 1 minute into the cephalic vein of the right forelimb of a female beagle (body weight: 10.6–12.6 kg). The tail of the female beagle was carefully shaved in advance with an electric shaver so as not to damage the skin. The area was cleaned with 70% alcohol and this was then used for blood pressure measurements. In other words, maximum blood pressure, minimum blood pressure and pulse pressure were measured over time by oscillometry using a BP-203NP Continuous Blood Pressure Monitor (Nihon Corine Ltd.).

For the control sample, an iloprost solution having a concentration 1/10th that of the above iloprost-dextran solution was prepared (50 ug/animal) and maximum blood pressure, minimum blood pressure and pulse pressure were measured in the same manner using this control solution.

Those results are indicated in FIG. 4.

In FIG. 4, —●— indicates maximum blood pressure, —△— indicates minimum blood pressure and —○— indicates pulse pressure.

According to FIG. 4, although iloprost, even at a concentration of 1/10th that of the sample solution, clearly demonstrates a transient decrease in blood pressure following administration, there were no fluctuations in blood pressure observed in the case of the iloprost-dextran complex.

EMBODIMENT 6

10 mg of prostaglandin $E_1$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of dextran (weight average molecular weight: 72,200, Farmacia Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for an additional 10 minutes in an ice bath. The colorless solid that precipitated was filtered under a reduced pressure. The filter cake was washed twice with 2 ml of distilled ethanol each time. This was then dried under reduced pressure at room temperature using $P_2O_5$ as the drying agent. Result: 42 volumes, 160 mg.

EMBODIMENT 7

10 mg of prostaglandin $E_2$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of dextran (weight average molecular weight: 72,200, Farmacia Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for an additional 10 minutes in an ice bath. The colorless solid that precipitated was filtered under reduced pressure. The filter cake was washed twice with 2 ml of distilled ethanol each. This was then dried under reduced pressure at room temperature using $P_2O_5$ as the drying agent. Result: 42 volumes, 150 mg.

EMBODIMENT 8

10 mg of prostaglandin $F_{2\alpha}$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of dextran (weight average molecular weight: 72,200, Farmacia Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for 10 minutes in an ice bath. The colorless solid that precipitated was filtered under reduced pressure. The filter cake was washed twice with 2 ml of distilled ethanol each time. This was then dried under reduced pressure at room temperature using $P_2O_5$ as the drying agent. Result: 47 volumes, 155 mg.

EMBODIMENT 9

10 mg of prostaglandin $E_1$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of pluran (weight average molecular weight: 50,000, Hayashibara Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for an additional 10 minutes in an ice bath. The colorless solid that precipitated was filtered under reduced pressure. The filter cake was washed twice with 2 ml of distilled ethanol each time. This was then dried under reduced pressure at room temperature using $P_2O_5$ as the drying agent. Result: 42 volumes, 150 mg.

EMBODIMENT 10

10 mg of prostaglandin $E_2$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of hydroxyethylated starch (HES', Sigma Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for an additional 10 minutes in an ice bath. The colorless solid that precipitated was filtered under reduced pressure. The filter cake was washed twice with 2 ml of distilled ethanol each. This was then dried under reduced pressure at room temperature using $P_2O_5$ as the drying agent. Result: 42 volumes, 155 mg.

EMBODIMENT 11

10 mg of prostaglandin $F_{2\alpha}$ and 9 mg of 1,1'-carbonyldiimidazole (CDI) were mixed in 1.2 ml of dimethylsulfoxide (DMSO) and stirred at room temperature for 15 minutes to form liquid (A).

Liquid (A) was then added over the course of roughly 30 seconds, while stirring, to a previously mixed solution of 170 mg of dextran (weight average molecular weight: 38,000, Farmacia Co.) and 0.5 mg of 4-pyrrolizinopyridine in 5 ml of DMSO and 0.5 ml of triethylamine ($Et_3N$). The mixture was then stirred as is for 3 days at room temperature.

20 ml of distilled ethanol was added to the reaction mixture while stirring and then stirred for an additional 10 minutes in an ice bath. The colorless solid that precipitated was filtered under reduced pressure. The filter cake was washed twice with 2 ml of distilled ethanol each time. This was then dried under reduced pressure at room temperature using $P_2O_5$ as the drying agent. Result: 47 volumes, 155 mg.

EXPERIMENTAL EXAMPLE 5

Confirmation of Bound Prostaglandins $E_1$, $E_2$ and $F_{2\alpha}$ in Prostaglandin $E_1$-, $E_2$- and $F_{2\alpha}$-Dextran Bonded Complexes by High-Pressure Liquid Chromatography As the prostaglandin $E_1$- and $E_2$-dextran bonded complexes are decomposed into free prostaglandin $E_1$ and prostaglandin $E_2$ by hydrolysis in a 0.1N solution of sodium hydroxide, confirmation of free prostaglandins $E_1$ and $E_2$ from the prostaglandin $E_1$- and $E_2$-dextran bonded complexes were confirmed by hydrolysis in buffered solutions at pH 10.0 and pH 9.0 as is indicated in the procedure below. In addition, confirmation of free prostaglandin $F_{2\alpha}$ following hydrolysis of the prostaglandin $F_{2\alpha}$-dextran bonded complex was performed with a 0.1N solution of sodium hydroxide.

10 mg of each of the prostaglandin $E_1$-, $E_2$- and $F_{2\alpha}$-dextran bonded complexes obtained in Embodiments 6, 7 and 8 were dissolved in 4.0 ml of water. This was followed by the addition of 1.0 ml of methanol to form sample solutions 1, 2 and 3.

Similarly, 10 mg of each of the prostaglandin $E_1$- and $E_2$-dextran bonded complexes obtained in Embodiments 6 and 7 were dissolved in 2.0 ml of water. This was followed by the addition of 2.0 ml of Briton Robinson buffer (pH 9.0 and 10.0 respectively) and 1.0 ml of methanol. These were then allowed to stand for 2 hours at 37° C. to form sample solutions 4 and 5. In addition, 10 mg of the prostaglandin $F_{2\alpha}$-dextran bonded complex obtained in Embodiment 8 was dissolved in 1.0 ml of water. This was followed by the addition of 2.0 ml of a 2N NaOH solution and 1.0 ml of methanol. This was then allowed to stand for 30 minutes at room temperature to form sample solution 6.

High-pressure liquid chromatography was then performed on sample solutions 1-6 in accordance with the conditions described to follow to confirm the presence of free prostaglandins $E_1$, $E_2$ and $F_{2\alpha}$ in each of the dextran bonded complexes.

The results are indicated in FIGS. 5, 6 and 7. FIGS. 5(a), 6(a) and 7(a) indicate the chromatograms for sample solutions 1, 2 and 3, and FIGS. 5(b), 6(b) and 7(b) indicate the chromatograms for sample solutions 4, 5 and 6. In other words, the results indicate that free prostaglandins $E_1$, $E_2$ and $F_{2\alpha}$ were not present in the prostaglandin $E_1$-, $E_2$- and $F_{2\alpha}$-dextran bonded complexes. In addition, free prostaglandin $E_1$, $E_2$ and $F_{2\alpha}$ were able to be confirmed following ester hydrolysis by alkali treatment of each of the bonded complexes.

HPLC Conditions:

Stationary Phase: Nucleosil $5C_{18}$ (5 μm) 4.6 mmφ×25cm

Mobile Phase: Acetonitrile - pH3 phosphate buffer (34:66)

Flow Rate: 2 ml/min

Detecting Wavelength: 210 nm

Injected Volume: 20 μl

EXPERIMENTAL EXAMPLE 6

Determination of the Amounts of Bound Prostaglandins $E_1$, $E_2$ and $F_{2\alpha}$ in the Prostaglandin $E_1$-, $E_2$- and $F_{2\alpha}$-Dextran Bonded Complexes by $^1$H-NMR When 2-3 mg of the $E_1$-, $E_2$- and $F_{2\alpha}$-dextran bonded complexes obtained in Embodiments 6, 7 and 8 were dissolved in 0.5 ml of $D_2O$ followed by measurement of $^1$H-NMR, a dextran-originating signal as well as signal characteristic of prostaglandins $E_1$, $E_2$ and $F_{2\alpha}$ were observed.

$\delta = 5.1$ ppm (1H, s, proton of anomer originating from dextran)

$\delta = 1.0$ ppm (3H, s, proton of methyl group bonded to a 20th order carbon originating from prostaglandins $E_1$, $E_2$ and $F_{2\alpha}$)

Based on the integrated values of the signals of the proton of the dextran anomer of the prostaglandin-dextran bonded complexes, and the proton of the methyl group at the side chain termini of prostaglandins $E_1$, $E_2$ and $F_{2\alpha}$, the number of bound prostaglandin $E_1$, $E_2$ and $F_{2\alpha}$ units y per 100 sugar units can be determined with the formula below:

$$y = \frac{\text{(Mol. wt. of polysaccharide)}}{\text{(Unit mol. wt. of polysaccharide)}} \times \frac{\text{(Integrated signal value of PG side chain terminal methyl)}}{3 \times \text{(Integrated signal value of anomer proton)}} \times 100$$

As a result of $^1$H-NMR measurement, the number of units of bound prostaglandins $E_1$, $E_2$ and $F_{2\alpha}$ per 100 sugar units was 0.75, 2.36 and 1.85, respectively.

EXPERIMENTAL EXAMPLE 7

Duration of Platelet Aggregation Inhibitory Effects of Prostaglandin $E_1$-Dextran Bonded Complex 12 mg of the prostaglandin $E_1$-dextran bonded complex obtained in Embodiment 6 was accurately weighed. Physiological saline was then added to accurately bring it to a volume of 20 ml to form the sample solution.

5 ml of the above sample solution was administered into the cephalic vein of the right front limb of a beagle (body weight: 11.3-11.9 kg) over the course of 1 minute. 4.5 ml of blood was then drawn over time into a syringe previously filled with 0.5 ml of 3.8% sodium citrate from the cephalic vein of the left front limb. 225 $\mu$l of the platelet-rich plasma (PRP) obtained by routine methods from the above beagle blood was placed in an aggregometer cell. Following incubation for 3 minutes at 37° C,. 25 ul of 300 uM of ADP was added and platelet aggregation was measured using an aggregometer.

The chronological transitions for inhibition of platelet aggregation following intravenous injection of the sample solution are indicated in FIG. 8.

For the control, 1.2 mg of prostaglandin $E_1$ was accurately weighed. Physiological saline was then added to accurately bring it to a volume of 20 ml to form the sample solution.

5 ml of the above sample solution was then administered into the cephalic vein of the right front limb of a beagle (body weight: 9.2-10.1 kg) over the course of 1 minute. Blood samples were then drawn over time in the same manner as in the case of the prostaglandin $E_1$-dextran bonded complex. The platelet aggregation of the blood obtained was then measured. The chronological transitions in the effectiveness of platelet aggregation inhibition following injection of prostaglandin $E_1$ (control) are indicated in FIG. 9.

From a comparison of FIG. 8 and FIG. 9, it was clear that the duration of the platelet aggregation inhibitory effects of the prostaglandin $E_1$-dextran bonded complex was greater than that of prostaglandin $E_1$.

EXPERIMENTAL EXAMPLE 8

Influence on Blood Pressure of Prostaglandin $E_2$ and Prostaglandin $E_2$-Dextran Bonded Complex 5 mg of the prostaglandin $E_2$-dextran bonded complex obtained in Embodiment 7 was accurately weighed. Physiological saline was then added to accurately bring to a volume of 10 ml to form the sample solution.

2 ml of the above sample solution was administered into the cephalic vein of one of the front limbs of a beagle (body weight: 9.2 kg) over the course of 30 seconds while anesthesizing by administration of 2 ml of 10% thiopental into the cephalic vein of the other front limb and forced inhalation of a mixed gas consisting of nitrous oxide and oxygen.

Next, the tail of the beagle was shaved in advanced using a shaver being careful so as not to damage the skin. The shaven area of the skin was then cleaned with 70% alcohol and this portion of the skin was used for measurement of blood pressure. That is, maximum and minimum blood pressure were measured over time by oscillometry using a model BP-203 Continuous Blood Pressure Monitor (Nihon Choline Co.). Those results are indicated in FIG. 10.

For the control sample, 200 $\mu$g of prostaglandin $E_2$ were accurately weighed. This was followed by the addition of physiological saline to accurately bring it to a volume of 20 ml. 0.5 ml of this control sample solution (corresponding to prostaglandin $E_2$ at a concentration 0.42 times that of the prostaglandin $E_2$-dextran bonded complex solution) was then administered into the cephalic vein of one of the front limbs of an anesthesized beagle (body weight: 10.1 kg) over the course of 30 seconds in the same manner as in the case of the above prostaglandin $E_2$-dextran bonded complex. Maximum and minimum blood pressure were then measured over time. Those results are indicated in FIG. 11.

As is clear from FIGS. 10 and 11, although prostaglandin $E_2$ resulted in a transient drop in blood pressure following administration, even at a concentration 0.42 times that of the prostaglandin $E_2$-dextran bonded complex solution, the prostaglandin $E_2$-dextran bonded complex demonstrated no observed fluctuations in blood pressure.

What is claimed is:

1. A stabilized prostaglandin composition comprising a prostaglandin compound selected from the group consisting of prostaglandin $E_1$, prostaglandin $E_2$, prostaglandin $F_{2\alpha}$, prostaglandin $I_2$, carbacycline and iloprost covalently bonded to a polysaccharide selected from the group consisting of pluran, amylose, amylopectin, cellulose, dextran and hydroxyethylated starch.

2. The composition of claim 1, in which 0.05 to 20 molecules of the prostaglandin compound are covalently bonded per 100 monosaccharide molecules of said polysaccharide.

3. The composition of claim 1, in which 0.05 to 5 molecules of the prostaglandin compound are covalently bonded per 100 monosaccharide molecules of said polysaccharide.

4. The composition of claim 1, in which the polysaccharide has a molecular weight in a range of from about 10,000 to 150,000.

5. The composition of claim 1, in which the prostaglandin compound is iloprost and the polysaccharide is dextran.

6. The composition of claim 1, in which the prostaglandin compound is iloprost and the polysaccharide is pluran.

7. The composition of claim 1, in which the prostaglandin compound is iloprost and the polysaccharide is hydroxyethylated starch.

8. The composition of claim 1, in which the prostaglandin compound is prostaglandin $E_1$ and the polysaccharide is dextran.

9. The composition of claim 1, in which the prostaglandin compound is prostaglandin $E_2$ and the polysaccharide is dextran.

10. The composition of claim 1, in which the prostaglandin compound is prostaglandin $F_{2\alpha}$ and the polysaccharide is dextran.

11. The composition of claim 1, in which the prostaglandin compound is prostaglandin $E_1$ and the polysaccharide is pluran.

12. The composition of claim 1, in which the prostaglandin compound is prostaglandin $E_2$ and the polysaccharide is hydroxyethylated starch.

* * * * *